United States Patent
Roe et al.

[11] Patent Number: 6,149,636
[45] Date of Patent: *Nov. 21, 2000

[54] DISPOSABLE ARTICLE HAVING PROACTIVE SENSORS

[75] Inventors: Donald C. Roe, West Chester, Ohio; Peter Coles, Francavilla al Mare, Italy; Mikhail K. Kruchinin, Cincinnati, Ohio; Simon S. Litvin, Brighton, Mass.; Oleg N. Khomjakov, Saint Petersburg, Russian Federation; Thomas J. Osborne, Jr., Cincinnati, Ohio

[73] Assignee: The Procter & Gamble Company, Cincinnati, Ohio

[*] Notice: This patent is subject to a terminal disclaimer.

[21] Appl. No.: 09/107,561

[22] Filed: Jun. 29, 1998

[51] Int. Cl.⁷ .................................................. A61F 13/15
[52] U.S. Cl. ...................... 604/361; 604/358; 604/359; 604/360; 604/362; 604/367; 604/378; 604/385.01; 604/385.101; 604/385.12
[58] Field of Search ................................. 604/361, 360, 604/359, 358, 362, 367, 378, 385.01, 385.101, 385.12

[56] References Cited

U.S. PATENT DOCUMENTS

| | | |
|---|---|---|
| 2,127,538 | 8/1938 | Seiger . |
| 2,926,667 | 3/1960 | Burger et al. . |
| 3,418,661 | 12/1968 | Allison et al. . |
| 3,814,101 | 6/1974 | Kozak . |
| 3,881,491 | 5/1975 | Whyte . |
| 3,921,232 | 11/1975 | Whyte . |
| 3,987,792 | 10/1976 | Hernandez et al. . |
| 4,022,211 | 5/1977 | Timons et al. . |
| 4,246,900 | 1/1981 | Schröder . |
| 4,335,722 | 6/1982 | Jackson . |
| 4,356,818 | 11/1982 | Macias et al. . |
| 4,401,712 | 8/1983 | Morrison . |
| 4,636,474 | 1/1987 | Ogura et al. . |
| 4,657,537 | 4/1987 | Zimmerer . |
| 4,681,577 | 7/1987 | Stern et al. . |
| 4,705,050 | 11/1987 | Markham . |
| 4,732,930 | 3/1988 | Tanaka et al. . |

(List continued on next page.)

FOREIGN PATENT DOCUMENTS

| | | |
|---|---|---|
| 0 286 374 | 10/1988 | European Pat. Off. . |
| 0 612 520 A2 | 8/1994 | European Pat. Off. . |
| 0 804 912 | 11/1997 | European Pat. Off. . |
| 0 804 913 | 11/1997 | European Pat. Off. . |
| 0 804 914 A1 | 11/1997 | European Pat. Off. . |
| 0 804 915 | 11/1997 | European Pat. Off. . |
| 0 804 916 | 11/1997 | European Pat. Off. . |
| 0 804 917 | 11/1997 | European Pat. Off. . |
| 0 806 194 | 11/1997 | European Pat. Off. . |
| 0 806 195 | 11/1997 | European Pat. Off. . |
| 0 815 818 A1 | 1/1998 | European Pat. Off. . |
| 39 21 784 A1 | 1/1991 | Germany . |
| 10-62369 | 3/1998 | Japan . |
| 1277558 | 11/1999 | Japan . |
| WO 92/02005 | 2/1992 | WIPO . |
| WO 94/24974 | 11/1994 | WIPO . |
| WO 95/00089 | 1/1995 | WIPO . |
| WO 95/00090 | 1/1995 | WIPO . |
| WO 95/32697 | 12/1995 | WIPO . |
| WO 95/32698 | 12/1995 | WIPO . |

(List continued on next page.)

OTHER PUBLICATIONS

Surface Electrodes in Perineal Electromyography, Urology, Oct. 1988, Vol. XXXII, No. 4, pp. 375–379.

Primary Examiner—John G. Weiss
Assistant Examiner—Miley Craig Peppers, III
Attorney, Agent, or Firm—Thomas J. Osborne; David M. Weirich; Jacobus C. Rasser

[57] ABSTRACT

A disposable article having a sensor that predicts an impending event such as an elimination of bodily waste. The article may also include an actuator that performs a responsive function when the sensor predicts the impending event.

29 Claims, 8 Drawing Sheets

U.S. PATENT DOCUMENTS

| | | |
|---|---|---|
| 4,747,166 | 5/1988 | Kuntz . |
| 4,753,645 | 6/1988 | Johnson . |
| 4,754,264 | 6/1988 | Okada et al. . |
| 4,776,331 | 10/1988 | Simjian . |
| 4,778,459 | 10/1988 | Fuisz . |
| 4,787,896 | 11/1988 | Houghton et al. . |
| 4,790,836 | 12/1988 | Brecher . |
| 4,796,014 | 1/1989 | Chia . |
| 4,842,593 | 6/1989 | Jordan et al. . |
| 4,852,578 | 8/1989 | Companion et al. . |
| 4,968,312 | 11/1990 | Khan . |
| 4,981,465 | 1/1991 | Ballan et al. . |
| 5,002,541 | 3/1991 | Conkling et al. . |
| 5,100,933 | 3/1992 | Tanaka et al. . |
| 5,103,835 | 4/1992 | Yamada et al. . |
| 5,118,607 | 6/1992 | Bignami et al. . |
| 5,181,905 | 1/1993 | Flam . |
| 5,264,830 | 11/1993 | Kline et al. . |
| 5,330,459 | 7/1994 | Lavon et al. . |
| 5,341,127 | 8/1994 | Smith . |
| 5,342,343 | 8/1994 | Kitaoka et al. . |
| 5,416,469 | 5/1995 | Colling . |
| 5,468,236 | 11/1995 | Everhart et al. . |
| 5,520,674 | 5/1996 | Lavon et al. . |
| 5,558,655 | 9/1996 | Jezzi et al. . |
| 5,568,128 | 10/1996 | Nair . |
| 5,582,604 | 12/1996 | Ahr et al. . |
| 5,607,417 | 3/1997 | Batich et al. . |
| 5,641,562 | 6/1997 | Larson et al. . |
| 5,643,241 | 7/1997 | Ahr et al. . |
| 5,649,914 | 7/1997 | Glaug et al. . |
| 5,653,862 | 8/1997 | Parris . |
| 5,658,268 | 8/1997 | Johns et al. . |
| 5,678,564 | 10/1997 | Lawrence et al. . |
| 5,681,298 | 10/1997 | Brunner et al. . |
| 5,702,376 | 12/1997 | Glaug et al. . |
| 5,702,428 | 12/1997 | Tippey et al. . |
| 5,722,931 | 3/1998 | Heaven . |
| 5,728,125 | 3/1998 | Salinas . |
| 5,733,272 | 3/1998 | Brunner et al. . |
| 5,736,590 | 4/1998 | Rasmussen . |
| 5,760,694 | 6/1998 | Nissim et al. . |
| 5,769,834 | 6/1998 | Reiter et al. . |
| 5,797,892 | 8/1998 | Glaug et al. . |
| 5,876,393 | 3/1999 | Ahr et al. . |

FOREIGN PATENT DOCUMENTS

| | | |
|---|---|---|
| WO 96/14813 | 5/1996 | WIPO . |
| WO 96/20681 | 7/1996 | WIPO . |
| WO 97/16149 | 5/1997 | WIPO . |
| WO 97/24150 | 7/1997 | WIPO . |
| WO 97/32542 | 9/1997 | WIPO . |
| WO 97/42613 | 11/1997 | WIPO . |
| WO 97/45082 | 12/1997 | WIPO . |
| WO 98/18505 | 5/1998 | WIPO . |
| WO 98/22063 | 5/1998 | WIPO . |
| WO 98/29079 | 7/1998 | WIPO . |
| WO 98/29501 | 7/1998 | WIPO . |
| WO 99/07317 | 2/1999 | WIPO . |

6,149,636

DISPOSABLE ARTICLE HAVING PROACTIVE SENSORS

FIELD OF THE INVENTION

The present invention relates to disposable articles and, more particularly, to disposable articles having proactive sensors that predict the occurrence of an event related to the wearer, the article, or the waste.

BACKGROUND OF THE INVENTION

Today, disposable articles, such as diapers, adult incontinence briefs, sanitary napkins and tampons, are widely used in infant and toddler care and in the care of incontinent adults as a means of containing, isolating and disposing of bodily wastes. These articles have generally replaced reusable, washable cloth garments as the preferred means for these applications because of their convenience and reliability. The disposable articles respond to a defecation, urination or discharge event by absorbing or containing bodily wastes deposited on the article. Some disposable articles also signal a defecation, urination or discharge event after it has occurred (e.g., wetness indicators, temperature change detection). The articles, however, do not predict when an event is about to occur and prepare the article, wearer or caregiver for the occurrence of the predicted event. Current disposable articles have absorbent material in a configuration ready for use at the time of application to the wearer or have a configuration that does not become available until the time of a discharge of bodily waste or shortly thereafter. Barrier cuffs, for example, are in position when the article is applied to the wearer. Signaling devices such as thermal or visual indicators signal a urination event only after the urination has begun. For example, known potty training devices, however, detect and signal the wearer once the defecation or urination has begun and do not give the wearer the ability to get to the bathroom in time to prevent an accident.

SUMMARY OF THE INVENTION

The present invention is directed to a disposable article that predicts the occurrence of an event related to the bodily waste, the wearer, the article, or a component or components thereof using a proactive sensor and responds to this prediction by performing a function on the article or the wearer to prepare for or to delay the occurrence of the predicted event, or by signaling the caretaker or the wearer that the predicted event is about to occur.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner. A preferred embodiment of an absorbent article of the present invention is a unitary disposable absorbent article, such as the diaper 20 shown in FIG. 1. As used herein, the term "diaper" refers to an absorbent article generally worn by infants and incontinent persons about the lower torso. The present invention is also applicable to other absorbent or non-absorbent articles such as incontinence briefs, incontinence undergarments, absorbent inserts, diaper holders and liners, colostomy bags for a natural or artficial anus, feminine hygiene garments, tampons, wipes, disposable towels, tissues, water absorbing articles, oil absorbing articles, spill cleanup bags, desiccant bags, disposable mops, bandages, therapeutic wraps, supports, disposable heating pads and the like.

Figure 1:
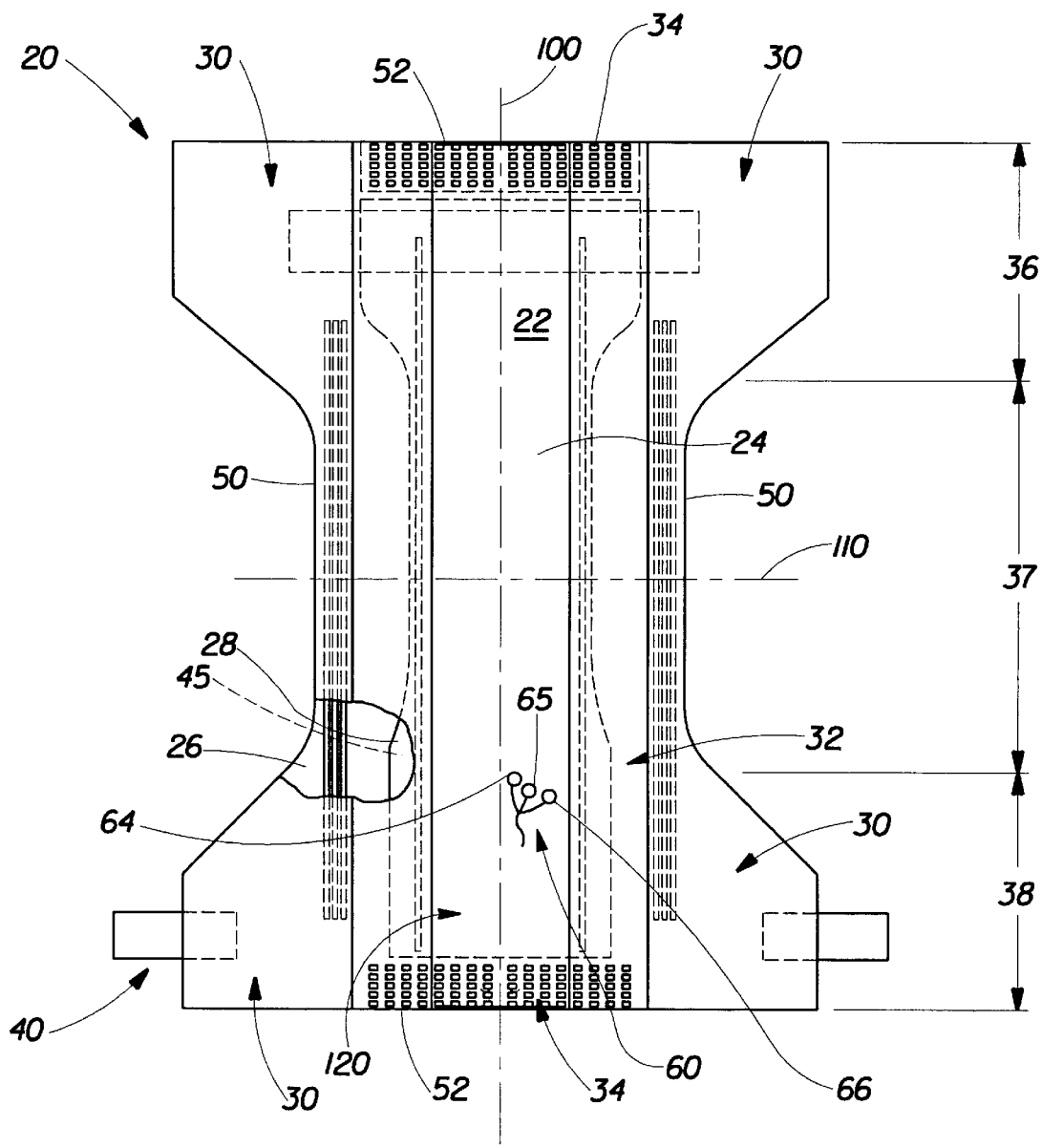
FIG. 1 is a plan view of the article made in accordance with the present invention in a flat-out state with portions of the structure being cut-away to more clearly show the construction of the article, wherein the article is a diaper.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; a fastening system generally designated 40 and a bodily waste isolation device 90. Diaper 20 is shown in FIG. 1 to have a first waist region 36, a second waist region 38 opposed to the first waist region 36 and a crotch region 37 located between the first waist region and the second waist region. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; each of which is incorporated herein by reference.

The backsheet 26 is generally that portion of the diaper 20 positioned adjacent the garment facing surface 45 of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials. The SELF web includes a strainable network having at least two contiguous, distinct, and dissimilar regions. Preferably, of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent the body surface 47 of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

The topsheet 24 is preferably compliant, soft feeling, and non-irritating to the wearer's skin. Further, at least a portion of the topsheet 24 is liquid pervious, permitting liquids to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the topsheets include fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 30 are made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, the topsheet 24 is made of a hydrophobic material or is treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein. Alternatively, the topsheet 24 may include an apertured web or film which is hydrophobic. This may be accomplished eliminating the hydrophilizing treatment step from the production process and/or applying a hydrophobic treatment to the topsheet 24, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The lotion may function alone or in combination with another agent as the hydrophobizing treatment described above. The topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the diaper 20.

Exemplary absorbent structures for use as the absorbent assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 62 of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also include a fastening system 40. The fastening system 40 preferably maintains the first waist region 36 and the second waist region 38 in an overlapping configuration so as to provide lateral tensions about the circumference of the diaper 20 to hold the diaper 20 on the wearer. The fastening system 40 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151, 092 issued to Buell on Sep. 9, 1992; and U.S. Pat. No. 5,221,274 issued to Buell on Jun. 22, 1993. The fastening system may also provide a means for holding the article in a disposal configuration as disclosed in U.S. Pat. No. 4,963, 140 issued to Robertson et al. on Oct. 16, 1990. Each of these patents is incorporated herein by reference. In alternative embodiments, opposing sides of the garment may be seamed or welded to form a pant. This allows the article to be used as a pull-on type diaper, such as a training pant.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaperer pulls one elasticized side panel 30 farther than the other during application, the diaper 20 will "self-adjust" during wear.

While the diaper 20 of the present invention preferably has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151, 092 issued to Buell on Sep. 9, 1992; and U.S. Pat. No.

5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/915,471 entitled "Absorbent Article With Multi-Directional Extensible Side Panels" filed Aug. 20, 1997 in the names of Robles, et al.; each of which is incorporated herein by reference.

The diaper 20 preferably further includes leg cuffs 32 which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition, issued Aug. 5, 1997 to Roe, et al. All of the above-cited references are hereby incorporated by reference herein.

The diaper 20 may also comprise one or more "proactive sensors" 60. As used in this application, the term "proactive sensor" refers to a sensor that is capable of detecting changes or signals in or on the body of the wearer, in the article or in the waste, i.e., inputs, that directly relate or, at a minimum, correlate to the occurrence of an impending event related to the bodily waste, the wearer, the article or a component or components thereof. Proactive sensors may respond to one or more specific inputs. Examples of inputs that may be detected by a proactive sensor of the present invention in order to predict an impending event include, but are not limited to, attitude, pressure, motion, vibration, contraction, tension, bloodflow, moisture, temperature, enzymes, bacteria, pH, conductivity, resistance, capacitance, inductance or other chemical, biochemical, biological, mechanical or electrical properties and/or components of bodily wastes. The sensor 60, for example, may be chemical, mechanical, electrical, thermal, etc. A chemical sensor may respond to chemical and/or biochemical inputs such as enzymes typically present in bodily wastes, pH, water, humidity or moisture, and/or biological inputs such as bacteria, blood or any other components of bodily wastes such as feces, urine, or menses, etc. Examples of chemical or biochemical sensors include dissolving or rupturable films, capsules, cells, seals, etc. that dissolve or rupture in response to a specific chemical, biochemical or biological input or to a specific class of chemical, biochemical or biological inputs. A mechanical sensor may also respond to motion, attitude, pressure, etc. An example of a mechanical sensor is a bellows-type sensor in which when the pelvic floor drops prior to defecation and the pressure pushes down on the bellows to inflate a portion of the sensor. A mechanical sensor may also include a sensor or a portion of the sensor that is broken or separated under a pre-defined applied pressure. An electrical sensor may also respond to moisture, urine, feces, menses, pressure, heat, temperature, conductance, resistance, capacitance, inductance, etc. An electrical sensor may, for example, include a sensor in which a conductive input such as urine completes an electrical circuit; a sensor in which an input such as pressure, tension or heat closes an electrical contact to complete a circuit; a piezoelectric sensor that generates a signal via pressure induced by the wearer or a part of the wearer (e.g., from motion or muscle tone); a sensor in which the resistance, capacitance or inductance varies in the presence of the input to which the sensor responds (e.g., conductance of the wearer's skin); or a sensor that receives electrical signals from the body (e.g., from the subcutaneous muscles) of the wearer through a contact such as a skin contact sensor. A thermal sensor may also be used to detect changes in temperature. Optionally, the sensor may be a biosensor as known in the art (e.g., an enzyme sensor, organella sensor, tissue sensor, microorganism sensor, or electrochemical sensor). The sensor may be adapted to detect proteins, sugars, bile components, etc. such as described in U.S. Pat. No. 4,636,474 entitled "Toilet Apparatus," issued to Kenji Ogura et al. on Jan. 13, 1987. Biosensors may comprise bio-recognition systems, typically enzymes or binding proteins such as antibodies immobilized onto the surface of physico-chemical transducers. The biosensors may detect components of bodily wastes, such as ammonia and phenol (e.g., via biosensors comprising enzyme electrodes). A specific strain of bacteria may be detected via biosensors employing antibodies raised against that bacterial strain. Exemplary enzyme electrodes that may be used to detect phenols (e.g. in urine or feces) include tyrosinase based electrodes or polyphenol oxidase enzyme electrodes described in U.S. Pat. No. 5,676,820 entitled "Remote Electrochemical Sensor," issued to Joseph Wang et al. on Oct. 14, 1997 and U.S. Pat. No. 5,091,299 entitled "An Enzyme Electrode For Use In Organic Solvents," issued to Anthony P. F. Turner et al. on Feb. 25, 1992, respectively.

Further, a sensor of the present invention may also be reversible or irreversible. A dissolving film or capsule is an example of an irreversible sensor, while an electrical sensor that receives electrical signals from the body of a wearer may receive multiple signals in succession.

A proactive sensor 60 may detect an impending event or detect a parameter that directly relates, or at a minimum correlates to the occurrence of an impending event. An impending event that may be detected or predicted by a proactive sensor 60 of the present invention may include, for example, urination, defecation, heat rash, skin irritation or rash, skin pressure marks, or an illness or medical condition of the wearer such as an internal infection (e.g., jaundice), a vitamin deficiency, a bile duct blockage, candidiasis, a parasite, a potential chronic skin condition or irritation, etc. A parameter that correlates to an event is any measurable input, signal such as one or more of the potential inputs listed above, that correlates with the occurrence of the event within the frame of reference of the system (i.e., a signal caused by the waste or the wearer). The proactive sensor 60 may, for example, predict the occurrence of a defecation, urination or discharge of bodily waste or may detect signals that may precede skin rash or irritation. Proactive sensors 60 in an article may measure many different inputs in order to predict an event. For example, the proactive sensor 60 may monitor the external anal sphincter muscle for a relaxation in the anal sphincter that precedes the release of feces and/or urine, a separation of the buttocks, a pressure change in the abdomen, a gas concentration in the article, a drop in the pelvic floor, or any other indication that may be used to predict or anticipate the occurrence of an event such as a defecation, a urination or a discharge of bodily wastes. Alternatively, a proactive sensor 60 of the present invention may detect signals that precede skin irritation. For example, the sensor may detect residual fecal contamination of the wearer's skin (e.g., fecal enzyme residue left on the wearer's skin after cleaning up a soiled diaper) that may, over time, lead to irritated skin. Detection of a high pH, an increased skin hydration resulting in a measurable increase in conductance or decrease in impedance of skin, a specific microorganism, fecal enzymes, etc. may also be used to predict potential skin irritation.

The proactive sensor 60 may be disposed in and/or operatively connected to any portion of a disposable article that will be exposed to the input that the sensor is designed to detect. For the purposes of the present invention, the term "operatively connected" refers to a means of communication such that the proactive sensor 60 may signal some portion of the article 20 when the proactive sensor 60 detects an input. The proactive sensor 60 may be separate from and operatively connected to another portion of the proactive sensor 60, another sensor 60, an actuator 70, a controller 80 or some other portion or component of the article 20. "Operatively connected" may, for example, include a means of communication such as an electrical connection via a conductive wire or member, via a transmitted signal such as radio frequency, infrared or another transmitted frequency communication. Alternatively, the sensor 60 may be operatively connected via a mechanical connection such as a pneumatic or a hydraulic connection.

In article 20, for example, the proactive sensor 60 may be located in the front waist region 36, the rear waist region 38 or the crotch region 37 of article 20, and may be integral with, disposed adjacent to, joined to, or comprise a portion of the chassis 22, the topsheet 24, the backsheet 26, the absorbent core 28, side panels 30, leg cuffs 32, a waist feature 34, a fastening system 40, the longitudinal 50 or end 52 edges, etc. The proactive sensor 60 may be integral with the article 20, or may be installed by the caretaker or the wearer. The proactive sensor 60 may be completely contained within the article such as article 20 or may have a receiving portion located in the article such that it will come into contact with the desired input and another portion such as a transmitting portion located either in the article or outside the article. The proactive sensor 60 may be external to the article 20 yet operatively connected to some portion of the article 20 such that the proactive sensor 60 may detect an input external to the article 20 and provide a signal to a controller 80 and/or an actuator 70. In some embodiments, the sensor may be separate from the article, e.g., separately applied to some portion of the wearer, and/or may have one or more component separate from the article.

The proactive sensor 60 may further comprise a sensing "system" including two or more sensors, each of which may detect the same or different signals from the same or different sources. The sensing system may include components that are located inside, external to and/or separate from the article. For example, the sensing system may include a sensor inside the article that detects electrical signals in the external anal sphincter of the wearer and a sensor external to the article that detects motion, tension or muscle activity in the abdomen of the wearer. The sensing system may also or alternatively include components other than the sensing elements inside, external to and/or separate from the article. The sensing system, for example, may include a transmitter that is external to the article and transmits a signal to another part of the sensing system that is joined to or disposed in the article 20.

The article 20 preferably also comprises an actuator 70. As used in this application, the term "actuator" refers to a device that comprises "potential" and a means of transforming that potential to perform or activate a "responsive function." The potential of the actuator 70 may comprise either stored or potential energy or stored material. The actuator 70 thus may perform or activate a responsive function by transforming potential energy to kinetic energy or by releasing or delivering a stored material. A "responsive function" is defined for the purposes of the present invention as a function performed upon the bodily waste, the wearer, the article, or a component or components thereof, or a signal to the wearer or the caretaker. A component of bodily waste may include, for example, moisture, electrolytes, enzymes, volatile gases, bacteria, blood, etc. A component of the wearer may also include skin, genitalia, the anus, the anal sphincter muscle, etc. A component of the article may also include leg cuffs, waist cuffs or other waste barriers and/or containment components, side panels, ears, a chassis, an absorbent core, an acquisition component, a fastening system, the longitudinal or end edges, etc. Potential energy may be stored as mechanical, electrical, chemical or thermal energy. "Kinetic energy" as used in this application refers to the capacity to do work or to perform a responsive function as described above (e.g., expansion of a compressed device, rotation of a twisted device, a gel that moves as it changes phases, coating or treatment of skin or feces, inhibition of an enzyme, adjustment of pH, etc.).

Triggering the creation of a three dimensional structure to capture waste, for example, involves responsive functions performed on a component of the article and, ultimately, on the waste. Capturing waste, wiping the skin of the wearer or treating the skin with a skin care composition, for example, are responsive functions performed on the waste and/or the wearer. Adjusting the article's geometry (in one, two or three dimensions) or physical properties (e.g., bending modulus, geometry, etc.) are examples of responsive functions, which may be performed on the article. Signaling a caretaker and/or the wearer that an event is about to occur is also considered a responsive function for the purposes of the present invention. An actuator of a disposable article may, for example, release or deliver a deodorant, enzyme inhibitor, skin care composition or pH control agent; capture, wipe, cover, trap, immobilize, seal, pump, or store bodily waste; or trigger the release or creation of a structure or element designed to perform one or more of these functions or any other responsive function upon the waste, wearer, article, or a component thereof.

An actuator 70 of the present invention may release potential energy to perform or activate a responsive function upon the waste, the wearer, the article, or a component thereof. The release of potential energy may transform mechanical, electrical, chemical or thermal potential energy into mechanical, electrical or chemical kinetic energy to perform the responsive function. Actuators may be triggered by a threshold level of an input to release potential energy to perform a responsive function or may respond continuously to an input as described below. For example, a compressed foam has stored compressive mechanical potential energy and may provide mechanical kinetic energy when it is released. A twisted foam has stored torsional mechanical potential energy that may provide mechanical kinetic energy, i.e., rotation, when it is released. In addition, stored chemical, electrical or thermal energy may be used to release electrical, mechanical, chemical or thermal kinetic energy. An actuator of a disposable article, for example, may include one or more of the following: stored lotion, feces modification agents, enzyme inhibitors, pH buffers, dyes, pressurized gas, a compressed foam, a twisted foam, a pump, a closed system liquid transport member, an electrically sensitive gel, a pH sensitive gel, a salt concentration gel, etc. Potential energy may be stored in any manner sufficient to maintain/restrain it until it is required. Examples include batteries and/or capacitors, elastically, torsionally, compressively tensioned materials or structures, in the form of unreacted reagents, and materials capable of performing physical or chemical functions (e.g., absorbents, emollients, pH buffers, enzyme inhibitors, feces modification agents; compressed gases, etc.).

Alternatively, an actuator 70 of the present invention may comprise a quantity of a stored material that has the capacity to perform or activate a responsive function upon the waste, the wearer, the article, or any component or components thereof. In one embodiment, for example, the actuator 70 may release or deliver a stored material that performs a responsive function. In this embodiment, the actuator 70 may be triggered by a threshold level of an input to discontinuously release or deliver the stored material at a given time or may release or deliver the material continuously. The actuator 70 may, for example, include stored lotion, skin care compositions, feces modification agents, enzyme inhibitors, pH buffers, dyes, etc. In certain preferred embodiments, the material may be delivered by an actuator 70 such as an expanding resilient material, a released high pressure gas, etc.

In alternative embodiments the sensor and/or actuator may comprise a closed system liquid transport member. A "closed system liquid transport member" or "transport member" comprises a liquid filled member having an inlet port and outlet port, which upon receipt of even a little amount of liquid at the inlet port practically immediately releases liquid at the outlet port. The liquid released from the outlet port may serve as an input signal to a sensor. For example, the liquid may be water, which is released when the transport member imbibes urine at an inlet port, which acts to dissolve a seal to release stored mechanical energy to create a feces void space. Alternatively, the transport member may itself trigger an actuator (e.g., mix with agents to perform a chemical reaction), or may perform at least a portion of the actuator function (e.g., the released water is imbibed by a super absorbent polymer arranged in a particular geometry, which swells and forms a feces void volume). Liquid transport through such transport members is based upon direct suction rather than on capillarity. The liquid is transported through a region into which no significant quantity of air (or other gas) may enter. The driving force for liquid flowing through such a member can be created by a liquid sink (e.g., a capillary or osmotic absorbent structure) or source in liquid connection with the member. Thus, a liquid transport member must have a relatively high liquid permeability There are preferably at least two regions within the transport member with different pore sizes, namely the one or more port region(s) having smaller pores and the inner region having a much larger pore size. The inner region of transport member has a permeability that is relatively high compared to the permeability of a port region (a higher liquid permeability provides less flow resistance), which can be a part of an outer/wall region circumscribing the inner/bulk region. Nonlimiting examples of high porosity materials suitable for use as the inner region material include fibrous structures comprising polyolefin, PET, cellulose, and cellulose-based fibers, and porous, open celled foam such as reticulated foams, cellulose sponges, polyurethane foams, and HIPE foams. In one embodiment, the voids of the inner region are essentially completely filled with an essentially incompressible fluid. The term "essentially completely" refers to the situation, where sufficient void volume of the inner region is filled with the liquid such that a continuous flow path between inlet and outlet ports can be established.

The port regions of the transport member comprise materials which are permeable for the transport liquid, but not for the ambient gas (like air) once they are wetted with the transport liquid. Often, such materials are described as membranes, which are defined as regions that are permeable for liquid, gas or a suspension of particles in a liquid or gas. The membrane may for example comprise a microporous region to provide liquid permeability through the capillaries. In an alternative embodiment, the membrane may comprise a monolithic region comprising a block-copolymer through which the liquid is transported via diffusion. Exemplary membranes for the port regions include celluloseacetate membranes, such as also disclosed in U.S. Pat. No. 5,108,383 entitled "Membranes For Absorbent Articles" issued to White on Apr. 28, 1992, PET films as disclosed in EP-A-0451797, nitrocellulose membranes, cellulosenitrate membranes, PTFE membranes, polyamide membranes, and polyester. Other suitable materials are woven polymeric meshes, such as polyamide or polyethylene meshes as available from Verseidag in Geldern-Waldbeck, Germany, or SEFAR in Rüschlikon, Switzerland.

Figure 9:
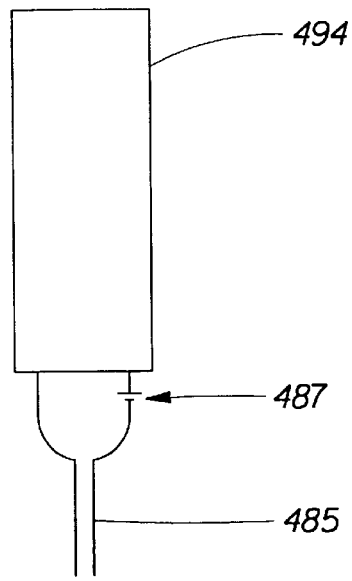
FIGS. 9 and 10 show an embodiment of a responsive system of the present invention including an electrically sensitive gel.
Figure 10:
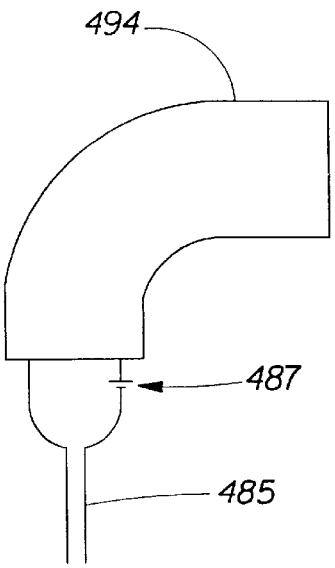
Figure 11A:
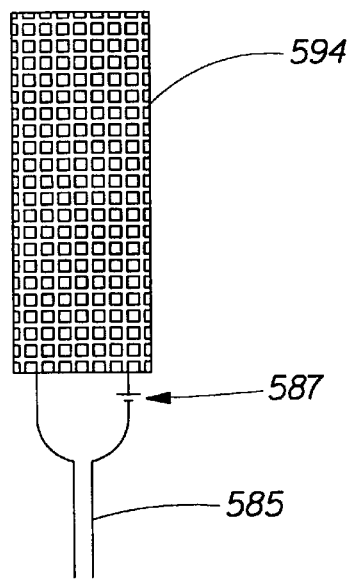
FIGS. 11A, 11B and 11C show another embodiment of a responsive system of the present invention including an electrically sensitive gel.
Figure 11B:
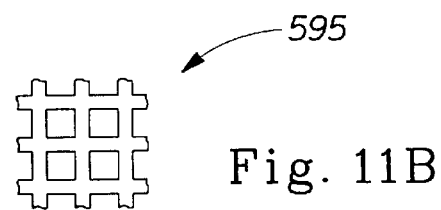
Figure 11C:
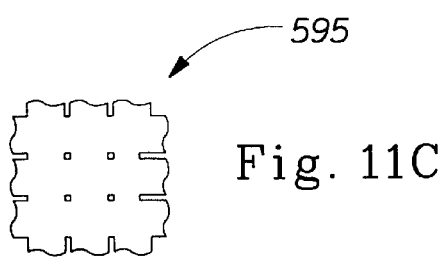

The actuator 70 may alternatively comprise an electrically sensitive gel. Electrically sensitive gels are polymeric gel networks that, when at least partially swollen with water, change volume and/or geometry under the application of an electric current or field. For example, certain partially ionized polyacrylamide gels will undergo anisotropic contraction of about 50% under weak electric fields (e.g., 0.5 volts/cm) when immersed in acetone and water. Alternative electrically sensitive gels may undergo electrically induced bending in the presence of water and a surfactant or may undergo an oscillating wave motion when subjected to an oscillating electric field. It is believed that local shrinkage may be induced in a portion of the gel, e.g., one side of a gel element, by concentrating positively charged surfactant molecules on the negatively charged gel polymer in an electric field. Changing the intensity and/or the polarity of the field induces a movement in the gel as one side decreases in length (e.g., a gel formed in a strip may curl). Electrically sensitive gels may comprise variable geometries such as rectangular, circular, reticulated grid, etc. patterns in order to provide a valve to release a material, allow a bodily waste to flow through, prevent a bodily waste from flowing through, encapsulate a bodily waste, etc. as they change volume and/or geometry. An electrically sensitive gel formed in a strip, for example, may be bent to provide an availiable void space for when electrical activity in the external anal sphincter muscle predictive of defecation or urination is detected. In FIGS. 9 and 10, for example, a strip of electrically sensitive gel 494 is shown in a circuit in which fecal moisture may bridge the contacts 485 and allow current to flow from battery 487 to the electrically sensitive gel either bending or straightening the strip. Alternatively, an electrically sensitive gel 494 formed in a reticulated grid pattern, such as shown in FIGS. 11A, 11B and 11C, may be electrically induced to swell or shrink when an imminent urination is detected to form a valve that allows and/or prevents urine flow to another portion of the article 20. FIG. 11A, for example, shows a circuit including a reticulated grid pattern of an electrically sensitive gel 594 . FIGS. 11B and 11C further show a microscopic view of the grid in a shrunk 593 and in a swollen 595 configuration, respectively. An exemplary material is a weakly cross-linked PAMPs gel (poly(acrylamido-2-methyl propane) sulphonic acid). This type of gel may perform various functions such as applying or delivering a chemical feces treatment agent. Other exemplary electrically sensitive gels are described in U.S. Pat. No. 5,100,933 issued to Tanaka on Mar. 31, 1990 and WO 9202005. Alternatively, pH sensitive gels or salt concentration sensitive gels that change volume and/or geometry at specific pH or salt concentrations, respectively, may be used as an actuator of the present invention.

The actuator 70 may be disposed in and/or operatively connected to any portion of disposable article that will allow the actuator to perform a responsive function upon the bodily waste, the wearer, the article, or a component thereof. In article 20, for example, the actuator 70 may be located in the front waist region 36, the rear waist region 38 or the crotch region 37 of article 20, and may be integral with, disposed adjacent to or joined to a component of the chassis 22, the topsheet 24, the backsheet 26, the absorbent core 28, side panels 30, leg cuffs 32, a waist feature 34, a fastening system 40, the longitudinal 50 or end 52 edges, etc. The actuator 70 may also be completely contained within the article such as article 20, may have a portion located in the article and a portion located outside the article 20, or may be completely external to the article 20. An actuator 70 or a portion of an actuator 70 may be operatively connected to one or more sensors 60, one or more controllers 80, another portion of the actuator 70 or another portion of the article 20. Further, the actuator 70 may be integral with the article 20, or may be installed by the caretaker or the wearer.

The article 20 may also include a controller 80. A "controller" is defined for the purposes of this application as a device that receives an input from a sensor and determines if one or more actions are to be taken. The controller may receive a signal from the sensor 60 and direct the actuator 70 to perform a responsive function upon the bodily waste, the wearer, the article or a component thereof. Alternatively, the actuator 70 may receive the signal directly from the sensor 60 and perform a responsive function upon the wearer, the waste, the article or a component thereof. A controller may include materials that undergo chemical or physical change, may be a chemical, mechanical or electrical device that processes information from a sensor, etc. For example, in an article having a compressed plastic foam material encapsulated and restrained under vacuum by a moisture soluble bag, the sensor 60 may comprise the moisture soluble bag. The physical and chemical characteristics of the film, i.e., the type of polymer, the thickness, etc., that determine how much of the input must be present before the film will dissolve act as the controller 80 and determine the threshold level of input that must be met before the controller 80 allows the actuator 70 to release stored energy to perform a responsive function. The actuator 70 is the combination of the compressed foam and the loss of vacuum, which allows release of the stored mechanical energy of the compressed foam. In this example, the controller 80 acts as a one-time switch. An electrical controller 80 that receives signals from the sensor 60 such as electrical activity of muscles of the wearer, however, may receive and monitor multiple electrical signals and may repeatedly trigger the actuator. The controller may be integral with the sensor component, integral with the actuator component, or a separate component of the system.

The controller 80 may be disposed in and/or operatively connected to any portion of a disposable article that will allow the controller 80 to receive a signal from the sensor 60 and to provide a signal to the actuator 70. In article 20, for example, the controller 80 may be located in the front waist region 36, the rear waist region 38 or the crotch region 37 of article 20, and may be integral with, disposed adjacent to or joined to the chassis 22, or a component of the topsheet 24, the backsheet 26, the absorbent core 28, side panels 30, leg cuffs 32, a waist feature 34, a fastening system 40, the longitudinal 50 or end 52 edges, etc. The controller 80 may be integral with the article 20, or may be installed by the caretaker or the wearer. The controller 80 may be completely contained within the article such as article 20, may have a portion located in the article and a portion located outside the article, or may be located completely outside the article 20. A controller 80 or a portion of a controller 80 may be operatively connected to one or more sensors 60, one or more actuators 70, another portion of the controller 80 or another portion of the article 20. The controller 80, for example, may receive a signal from the sensor 60 and provide a signal to the actuator 70, e.g., by a radio frequency (rf) transmission.

Although distinct structural elements may perform the sensor 60, actuator 70 and controller 80 functions, the sensor 60, actuator 70 and/or controller 80 functions of the present invention need not be performed by distinct structural elements. The sensor 60 and controller 80 functions, for example, may be performed by the same structural element such as a film that dissolves in contact with a component of a bodily waste. In this example, the film acts as a sensor and responds to the input component of bodily waste. The physical and chemical characteristics of the film, i.e., the type of polymer, the thickness, etc., that determine how much of the input must be present before the film will dissolve act as the controller and determine the threshold level of input that must be met before the controller allows the actuator to release stored energy to perform a responsive function.

A "responsive system" is defined for the purposes of this application as a system that includes a sensor 60 and an actuator 70 that acts upon the bodily waste, the wearer, the article, or a component or components thereof when the sensor 60 detects the appropriate triggering input. Upon sensing a given input parameter, the actuator 70 effects the release of stored energy or the release or delivery of stored material to perform a responsive function. When the proactive sensor 60 detects an impending event, the actuator effects the release of stored energy. By detecting an input signal prior to the impending event, a responsive system in the article may be triggered to prepare for the event or to signal the caregiver or the wearer of the impending event. This allows construction of articles in which the waste-management technology is initially "hidden" or unobtrusive, but which is available at, or just before, the moment of need and/or in which the article may provide the caregiver or the wearer the opportunity to prepare for an event in advance. Regardless of the specific input, the proactive sensor 60 in these embodiments may trigger an actuator to perform an action on the article, the wearer or the environment to prepare for the occurrence of the event or provide a signal to the caregiver that the impending event is about to occur. For example, if an impending defecation or urination is to be detected via the electrical activity of the external anal sphincter muscles, the system is preferably triggered (i.e., the responsive system is activated) by a signal related to relaxation of the anal sphincter. The actuator may then perform a function such as treating the wearer's skin to prevent or minimize skin irritation; preparing a bodily waste management device by activating a fecal void spacer; opening a valve to allow urine to flow into a storage device; releasing an enzyme inhibitor, skin care composition, pH control agent, or other skin treatment aids as known in the art; or providing an audible or visual warning signal to the caregiver or the wearer. If the sensor 60 comprises a sensing system, one actuator may be triggered by different sensors and/or signals, or different actuators may be triggered by different sensors and/or signals. Alternatively, one sensor and/or signal may trigger multiple actuators.

A responsive system may respond in either a "continuous" or a "discontinuous" manner. As used in this application, a "continuous responsive system" refers to a responsive system in which the output is quantitatively dependent upon the quantity of the input, i.e., continuously increasing quantities of the input are required to effect continuously increasing quantities of the output, or where the output of the responsive system comprises a passive release of a stored material. A super absorbent polymer placed in an absorbent core of an article, for example, provides a continuous response in which the output is quantitatively dependent upon the quantity of the input, i.e., as increasing quantities of liquid waste contact the super absorbent polymer, an increasing amount of the polymer contains that liquid until the capacity of the polymer is exhausted. A stoichiometric chemical reaction is another example of a system having a continuous response to increasing output. In the reaction A+excess B→C, for example, the amount of excess B converted to C is stoichiometrically and, therefore "continuously," related to the amount of A available in the system. One example of a continuous responsive system in which an inflatable spacer inflates to provide a void volume to store feces via a stoichiometric chemical reaction when a liquid such as urine contacts a gas evolving material, i.e., a continuous responsive system, is described in U.S. Pat. No. 5,330,459 entitled "Disposable Absorbent Article Having An Inflatable Spacer," issued to Gary D. Lavon et al. on Jul. 19, 1994. Another example of a continuous responsive system in which a disposable article that improves the fit on the wearer by a liquid such as urine dissolving a film to release a leg cuff that has been held in an expanded state is described in U.S. Pat. No. 4,246,900 entitled "Diaper Including Moisture-responsive Seal Means," issued to Schröder et al. on Jan. 27, 1981. A responsive system that passively releases a stored material, however, generally provides a continuous response regardless of how the material itself is released because the actual responsive function performed upon the bodily waste, the wearer, the article, or a component thereof is performed by the material, not by the release of the material. Thus, whether the material is released continuously in response to a given input, or released discontinuously at a single time when a threshold of a given input is detected, the responsive function performed by the released material is performed such that continuously increasing quantities of the input are required to effect continuously increasing quantities of the output until the material released is exhausted.

Figure 7A:
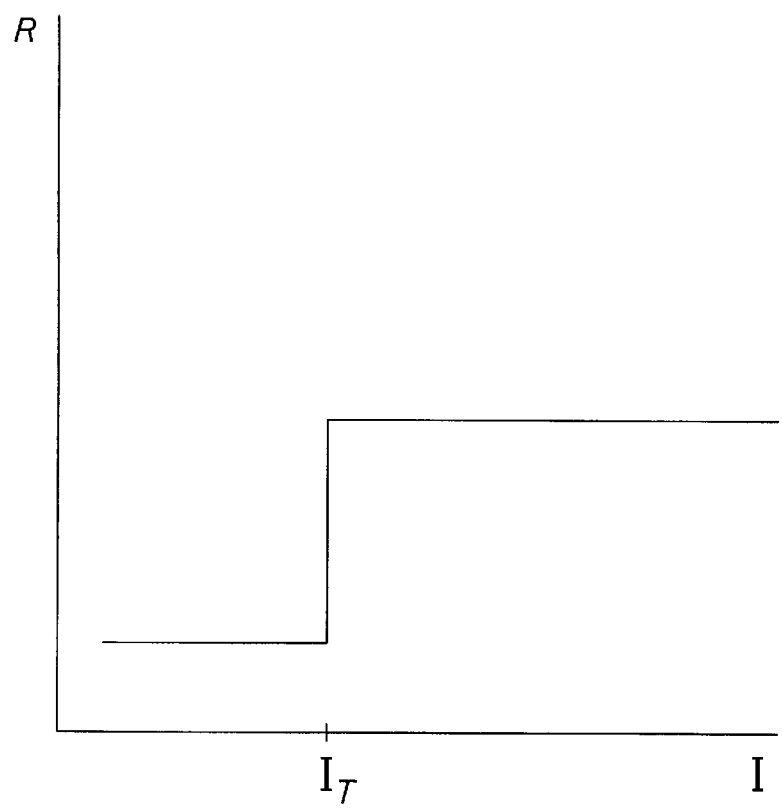
FIG. 7A shows an ideal output function of a discontinuous responsive system of the present invention having a single threshold level.

A "discontinuous responsive system" of the present invention, however, refers to a responsive system that has an output function that is essentially independent of the quantity of the input beyond a threshold level. For example, when one or more threshold levels of a given input are met, the responsive system may release all or a pre-designated portion of its stored energy or deliver, i.e., actively transport, all or a pre-designated portion of its stored material to perform a specific responsive function. In an ideal embodiment of the present invention, the output function, f(x), includes a "step" function as shown in FIG. 7A. In this embodiment, the rate of change in the output with increasing levels of input (d(output)/d(input)), i.e., the slope or first derivative f'(x) of the output function f(x), is preferably essentially zero when the amount of input is above or below the threshold level. At the threshold level, however, the d(output)/d(input) rate of change preferably approaches infinity. Thus, in the ideal discontinuous response, the limit of the function f(x−ε) as ε→0 is not equal to the limit of the function f(x+ε) as ε=0, i.e., lim f(x−ε)≠lim f(x+ε).

$$\epsilon \rightarrow 0 \quad \epsilon = 0$$

Figure 8A:
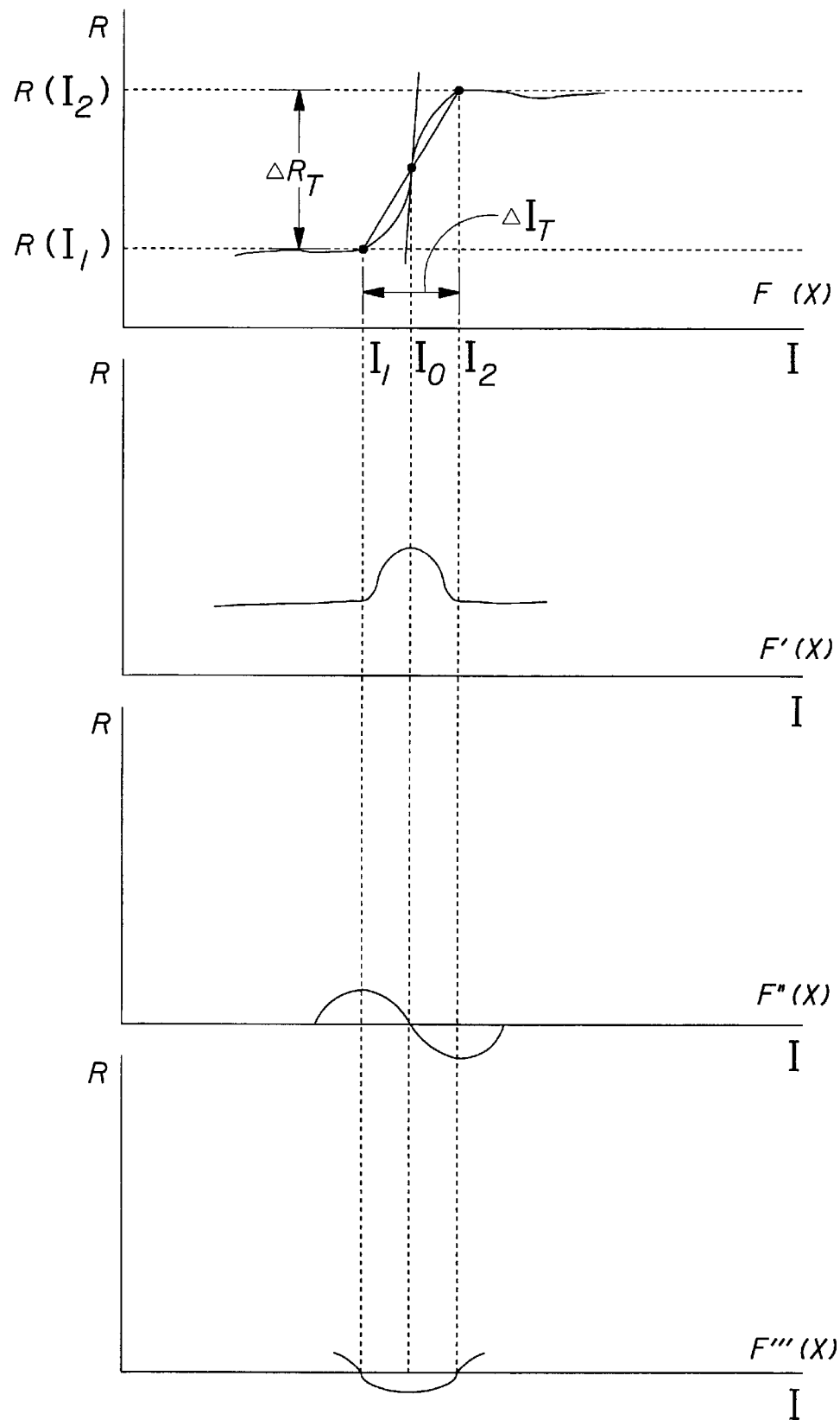
FIG. 8A shows an exemplary output function of a discontinuous responsive system of the present invention along with the first, second and third derivatives of the output function.

The present invention, however, recognizes that in the physical world an ideal instantaneous step change at the threshold level is not necessary and may not even be possible in many instances. In a preferred embodiment, it is only necessary that the output function have a virtual step change with very little change in the input at or around the threshold level of the input. Thus, the present invention contemplates a discontinuous responsive system of the present invention having an output function that responds in a sufficiently discontinuous manner in the transition region such that the output function has at least a minimum relative degree of steepness in the transition region. While not wishing to be limited to a particular method of describing or modeling a discontinuous system, in a preferred method of determining whether a given output function performs in a sufficiently discontinuous manner as defined for the purposes of the present invention, the slope of the output curve at the inflection point is compared with the relative slope of a line between the first and last points of the transition region. For example, FIG. 8A shows a graph of an exemplary output function, f(x) along with aligned graphs of the first, f'(x), and second, f"(x), and third, f'''(x), derivatives of the exemplary output function. The output function f(x) describes the effect of the in put (x or I) on the output or response (R(I)). For purposes of the present invention, the transition region is defined as the region between the relative maxima, $R(I_1)$, and the minima, $R(I_2)$, of the second derivative, f''(x), of the output function, f(x). The relative maxima, $R(I_1)$, and the relative minima, $R(I_2)$, are points at which the third derivative, f'''(x), equals zero. The inflection point, $I_0$, is defined as the point in the transition region at which the second derivative, f''(x), equals zero, i.e., $$\left.\frac{d^2 R}{d I^2}\right|_{I=I_0} = 0.$$

The comparison of the slope of the output function at the inflection point to the slope of a line between the first and the last points of the transition region can be described by the equation:

$$\left.\frac{d R}{d I}\right|_{I=I_0} = k \frac{(\Delta R_T)}{(\Delta I_T)}.$$

In this equation dR/dI at the inflection point is the first derivative of the output function at that point. The term $\Delta I_T$ is the change in the input to the responsive system between the first, $I_1$, and last, $I_2$, points of the transition region, i.e., $I_2 - I_1$, and the term $\Delta R_T$ is the change in the response of the output function between the first and last points of the transition region, i.e., $R(I_2) - R(I_1)$. The coefficient k is a proportional constant that describes the relative steepness of the slope of the output function at the inflection point, $I_0$, compared to the slope of a line between the first and last points of the transition region. In order that the responsive system have a discontinuous output function, the proportional constant k must be at least about 2.0, preferably at least about 3.0, more preferably at least about 5.0, even more preferably at least about 10.0, with at least about 100.0 being the most preferred.

Figure 8B:
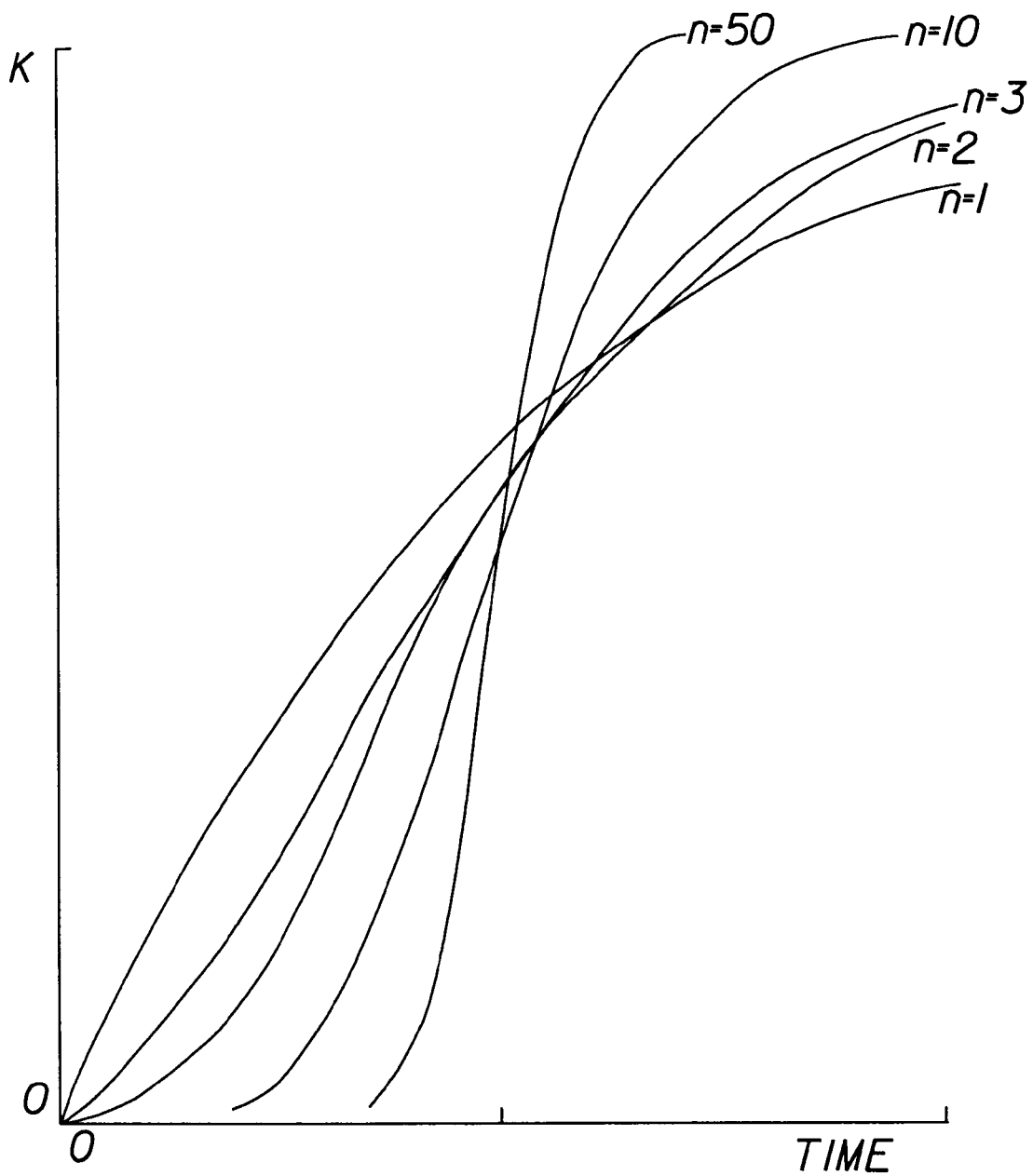
FIG. 8B shows a transfer function of a control system having a series of first order lags having an equal time constant.

In certain embodiments, the relative degree of steepness in the transition region of a discontinuous responsive system may also be modeled by a transfer function of a control system having a series of an integer number, n, first order lags with an equal time constant. The transfer function of the responsive system is defined for the purposes of the present invention as the ratio of the Laplace transforms of the output (responding variable) to the input (disturbing variable). See, e.g., Robert H. Perry & Don Green, *Perry's Chemical Engineers' Handbook*, Sixth Ed., Chap. 22 (McGraw Hill, Inc. 1984). As shown in FIG. 8B, the relative degree of steepness of an output function may be approximated by the formula: $KG(s)=K/(Ts+1)^n$ in which KG(s) is the transfer function, K is a proportional element, T is the time constant of the system, and n is the integer number of first order time lags. In this model, as the number n increases, the steepness of the output function in the transition region increases, and the model begins to approximate a discontinuous responsive system. Certain discontinuous responsive systems of the present invention preferably may be modeled by the above formula when n is greater than or equal to about 25, with n being greater than or equal to about 50 being more preferred, and n being greater than or equal to about 100 being the most preferred.

As shown in FIG. 7A, a responsive system of the present invention may include a single threshold level at which the responsive system may release all of its stored energy to perform a specific responsive function or may include multiple threshold levels at which the system may release a pre-designated portion of its stored energy to perform one or more specific responsive functions at each of the threshold levels. In an embodiment having a single threshold level, for example, the responsive system may release all of its stored energy to perform the entire responsive function when that threshold level is met. In such a single threshold embodiment, In this example, the discontinuous responsive system includes a system that has two states such as on or off. When a threshold quantity of an input such as bodily waste is present in the absorbent article, the responsive system may perform a single responsive function upon the waste, the wearer, the article or a component thereof, such as enveloping the waste away from the skin of the user. Thus, the discontinuous responsive system may perform a one-time "switch-like" function that changes from one state to another in the presence of a threshold level of an input.

Figure 7B:
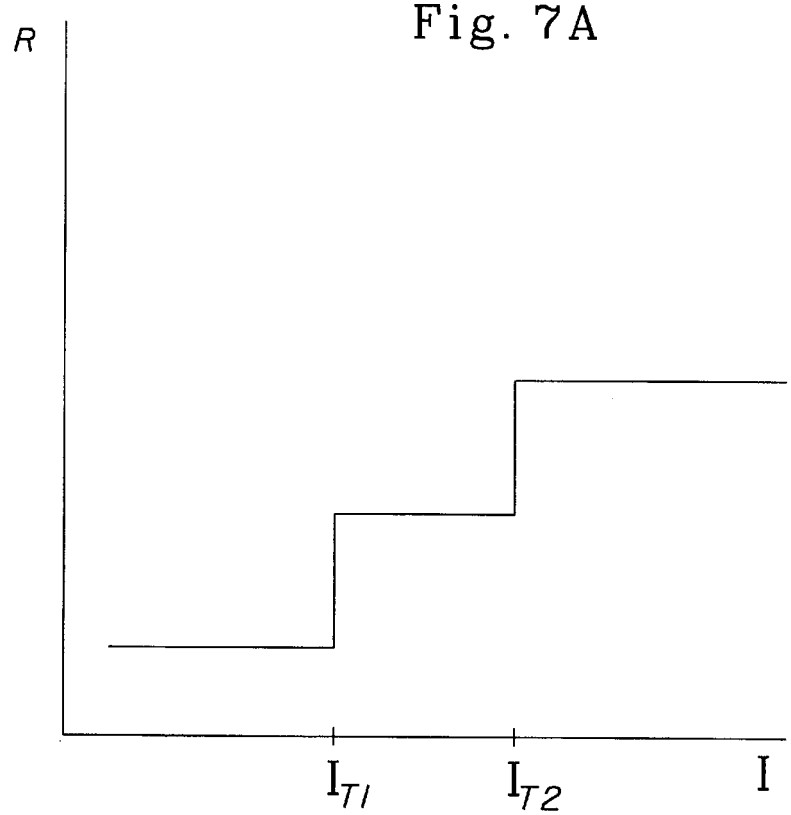
FIG. 7B shows an ideal output function of a discontinuous responsive system of the present invention having multiple threshold levels.

Alternatively, as shown in FIG. 7B, the responsive system may have multiple threshold levels such as It1 and It2 at which when each threshold level is met the system may release a given "quanta" of energy or deliver a given quantity of material to perform a specific responsive function. In this embodiment, when each threshold level is met, a portion of the entire responsive function may be performed and/or different independent responsive functions may be performed in response to different threshold levels being met. For example, a responsive system may monitor a fecal enzyme and when each threshold enzyme level is met may deliver an equal or unequal quantity of enzyme inhibitor(s) or lotion, or deliver a pH buffer at the first threshold level and perform another responsive function such as delivering a quantity of enzyme inhibitor(s) at the second threshold level. In each transition region, the responsive system responds essentially the same as the transition region in the single threshold embodiment described above.

In addition, a responsive system may monitor multiple inputs such as moisture and/or one or more fecal enzymes and perform one or more responsive functions when the threshold levels of the different inputs are met or may perform one responsive function only when two or more of the threshold levels of the different inputs are met. Thus, a controller may monitor multiple different inputs and perform a different responsive function when the threshold level of the different inputs are met. Alternatively, the controller may perform a logic OR-gate type function such that a responsive function may be performed when one or more threshold levels of the multiple inputs are met. The controller may also perform a logic AND-gate type function such that a responsive function may be performed when each threshold level of two or more different inputs is met.

Figure 6A:
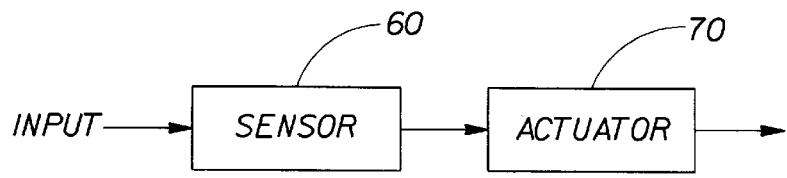
FIG. 6A shows a block diagram of an exemplary open loop responsive system.
Figure 6B:
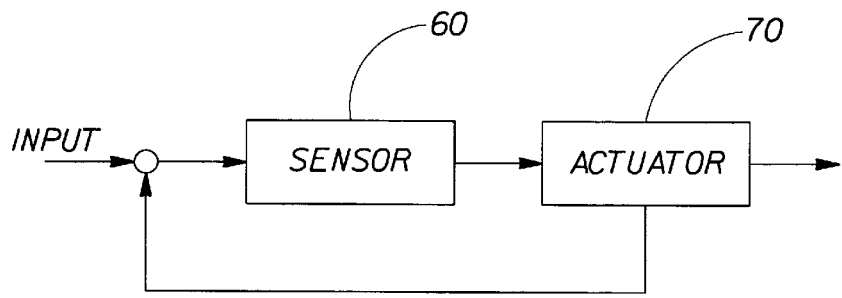
FIG. 6B shows a block diagram of an exemplary closed loop responsive system.
Figure 6C:
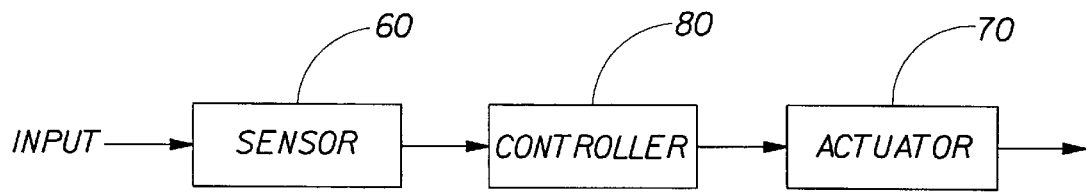
FIG. 6C shows a block diagram of an exemplary open loop responsive system including a controller.
Figure 6D:
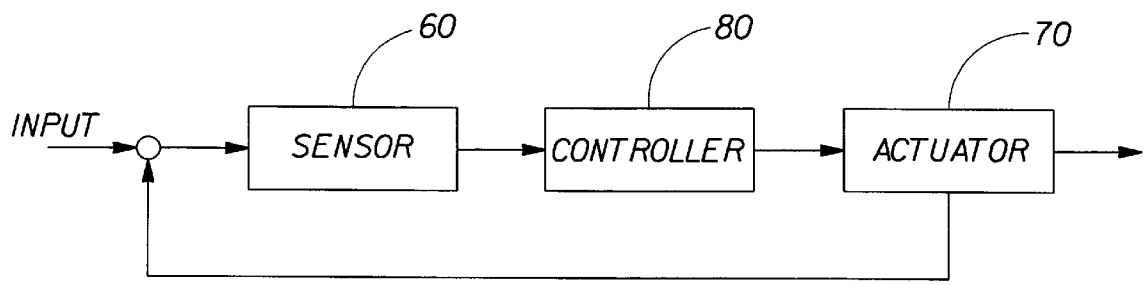
FIG. 6D shows a block diagram of an exemplary closed loop responsive system including a controller.

The responsive system may also comprise a "closed loop" or an "open loop" system. A "closed loop" system, which is also referred to as a "feedback control loop" system, includes distinct sensor 60 and actuator 70 components and performs a responsive function upon the input. In some preferred embodiments, the system may also use a detection or a measurement of an element or a parameter of the output condition as at least one trigger of the responsive function that is performed upon the input. The output condition may be the state of the input condition after the actuator 70 has had the opportunity to perform a responsive function on the input condition. For example, if the sensor 60 is monitoring the hydration level of the skin and the hydration level reaches a threshold level, i.e., the output condition of the responsive system, the responsive system may release a predetermined quantity of a desiccant to bring the hydration of the skin back to the desired target hydration or hydration range or may release a desiccant until the hydration returns to the target hydration or the hydration range. An absorbent material such as a super absorbent polymer that continually absorbs a liquid input until the liquid has all been absorbed or the capacity of the polymer has been reached, however, is not considered to comprise a closed loop system because the absorbent material does not have distinct sensor 60 and actuator 70 components. The responsive function may be performed when the output condition reaches a threshold level, or may be performed only when the output condition and one or more other conditions are met. Acting upon the input may include acting upon the element sensed, e.g., sensing pH and acting upon the pH or may include acting upon a composition of which the element sensed is an integral component, e.g., sensing a fecal enzyme or fecal moisture and acting upon feces. As described above, a feedback control loop system includes at least two distinct components: the sensor 60 and the actuator 70. A block diagram of an exemplary feedback control loop including a sensor 60 and an actuator 70 is shown in FIG. 6B. The sensor 60 detects an event, or a parameter associated with that event. The actuator 70 receives a signal and performs a responsive function on the input condition detected by the sensor 60. The feedback control loop may further include a controller 80. A block diagram of an exemplary feedback control loop including a sensor 60, an actuator 70 and a controller 80 is shown in FIG. 6D. In this case, the sensor 60 may provide a signal to the controller 80, and the controller 80 may direct the actuator 70 to perform a responsive function upon the input condition. The controller 80 may be a separate component of the responsive system or the controller function may be performed by the sensor 60 and/or the actuator 70.

The feedback control loop may be "non-modulating" or "modulating." In a "non-modulating" feedback control loop responsive system the responsive system acts as a one-time switch in which the actuator performs a responsive function on the input when the threshold level of the output condition is met. For example, the sensor 60 may detect a specific microorganism, and the actuator 70 may signal the caretaker of a potential incipient infection. In this example, the actuator 70 acts upon the input detected by the sensor 60. If the sensor 60 detects electrical signals in the anal sphincter of the wearer to predict an imminent defecation and the actuator 70 releases a compressed foam material to create a shaped void of sufficient volume to contain feces, however, the actuator 70 acts upon something other than the input detected by the sensor 60, i.e., acts upon the feces instead of the electrical activity in the sphincter muscles and is therefore not a feedback control loop. A "modulating" feedback control loop, however, includes a sensor 60, an actuator 70 and a controller 80. In a modulating feedback control loop, the output condition is monitored constantly or repeatedly, and the controller 80 directs the actuator to perform a responsive finction on the input in order to maintain the output condition at a desired set point or within a desired range. A modulating responsive system may constantly or repeatedly measure sphincter muscle electrical activity and send a signal to the sphincter muscles to keep the anal sphincter closed for a desired period of time to provide a feedback control loop responsive system.

An "open loop" system, however, is a system that responds to the input to perform a responsive function without using feedback, i.e., the output has no effect upon the sensed input entering the system. A block diagram of an exemplary open loop system including a sensor 60 and an actuator 70 is shown in FIG. 6A. A block diagram of an alternative open loop system further including a controller 80 is shown in FIG. 6C. An open loop system may include a responsive system that has a single device that performs the functions of both the sensor 60 and the actuator 70 or may have distinct sensor 60 and actuator 70 components in which the actuator acts upon something other than the input. A super absorbent polymer placed in an absorbent core of a disposable absorbent article, for example, provides an open loop response because the polymer only includes a single device that performs the functions of the sensor 60 and actuator 70. Alternatively, an open loop responsive system may include a sensor 60 that detects bodily waste or a component of that bodily waste, and an actuator 70 that performs a responsive function in a continuous or a discontinuous manner on something other than the input detected by the sensor 60. As above, for example, the sensor 60 may detect sphincter muscle electrical activity, and the actuator 70 may capture or store feces.

Other responsive systems are described in U.S. patent application Ser. Nos. 09/106,424 entitled "Disposable Article Having A Discontinuous Responsive System" filed on Jun. 29, 1998 (P&G Case Number 7197); 09/107,563 entitled "Disposable Article Having A Responsive System Including A Feedback Control Loop" filed on Jun. 29, 1998 (P&G Case Number 7198); and 09/106,225 entitled "Disposable Article Having A Responsive System Including A Mechanical Actuator" filed on Jun. 29, 1998 (P&G Case Number 7199), each of which is incorporated herein by reference.

An example of a diaper 20 of the present invention including a responsive system that includes a proactive sensor is shown in FIG. 1. In this embodiment, a skin contact sensor system comprises an electrical sensor 60 that includes three electrodes 64, 65 and 66. An electrical sensor 60 of the present invention may include two or more electrodes. In one embodiment, electrodes 64 and 65 may be active and electrode 66 may be a reference electrode. This allows for a bimodal electrical pickup. The skin contact sensor system may be releasably secured to the skin of the wearer in order to receive electrical signals from a muscle or muscle group of the wearer. For example, the skin contact sensor may be placed as close as possible to the anus of the wearer so that the probe may detect signals from the external anal sphincter muscle, which is anatomically near the skin at the point of the anal orifice. Preferably, an electroconductive, adhesive gel is placed on the electrode of the skin contact probe before it is placed on the skin. In this embodiment, the skin contact sensors may be placed on the wearer by the caretaker, or may be integral with the article such that they are automatically aligned and attached to the wearer's skin near the anal perimeter when the article is placed on the wearer. A 7 mm surface electrode manufactured by Dantec Medical A/S of Skovlunde, Denmark, which may be connected to a Dantec EMG (Type 14 D11) receiver unit, for example, is believed to be useful for the present invention. In this example, the Dantec EMG unit may be set, for example, at a time base of 20 msec/division resulting in a screen sweep time of 0.2 seconds. The gain amplifier may be set at 20 $\mu$V/division. A proactive sensor in this embodiment may vary in size and manufacture and may optionally be integral with the body of the article. The unit that receives the signal from the sensor(s) may be separate from the article or may be integral with the article. If the receiver unit is separate from the article, the article may additionally comprise a transmitter to transmit the signal to the receiver. This may be accomplished, for example, via an infrared (IR)

telemetry device. The settings for the sensor, transmitter (if required), and receiver may vary according to the specific type of signal, sensor embodiment, and function to be performed.

The surface electrodes 64, 65 and 66 of the skin contact sensor system in the above embodiment measure electrical signals in a muscle fiber or a group of muscle fibers. If the electrodes measure the electrical activity of a group of muscle fibers, the total potential change involves a greater mixture of frequencies. Preferably, the electrodes utilize two active electrodes 64 and 65 and one reference electrode 66 for a bimodal electrical pickup. The electrical activity measured by the surface electrodes includes a combination of EMG signals, other physiologic signals present on the skin surface such as EKG and electrodermal activity, and environmental artifacts such as 60 Hz from electronic equipment or radio frequency interference. When bimodal electrodes are used in combination with a differential amplifier, only those signals which are not detected in common by the two active electrodes are allowed to pass. Because a substantial portion of the common mode signals picked up by the electrodes are not EMG signals, it may be advantageous to reject signals common to both active electrodes. This common mode rejection provides a cleaner, more discrete signal from the sensor. For embodiments in which an imminent defecation or urination is to be detected via the electrical activity of the external anal sphincter muscles, the proactive sensor 60 preferably responds to a signal related to relaxation of the anal sphincter. Generally, the electrical activity of these muscles will drop sharply for at least several seconds as the muscles relax. The activity is close to zero immediately preceding and during the elimination process. In these embodiments, a sensor 60 may be triggered by precipitous drops in muscle electrical activity, preferably drops of greater than or equal to about 50%. More preferably, the sensor 60 may be triggered by drops of greater than or equal to about 75%, with greater than or equal to about 95% being the most preferred.

Figure 2:
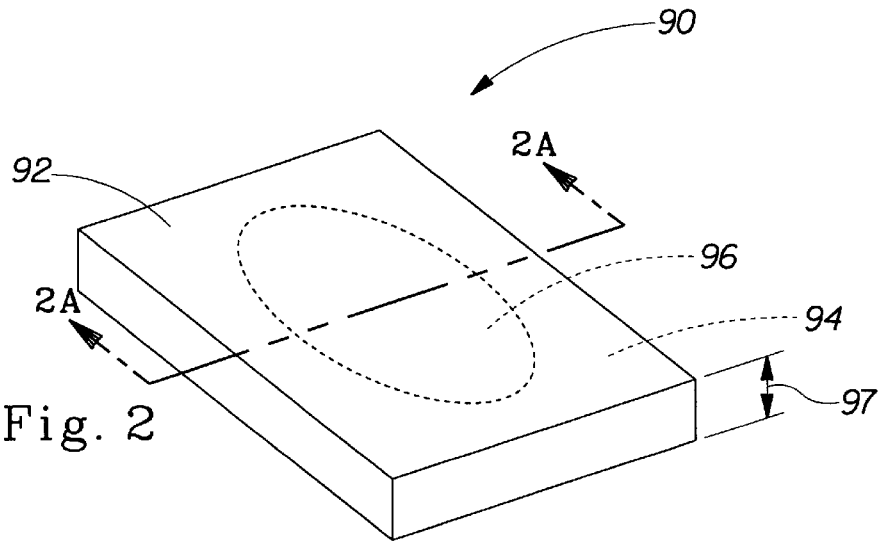
FIG. 2 shows a perspective view of a bodily waste isolation device of the present invention in a compressed state before activation.
Figure 2A:
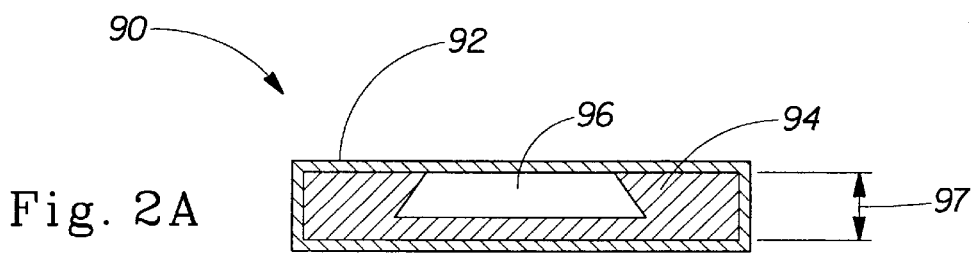
FIG. 2A shows a sectional view taken along line 2A—2A of FIG. 2.
Figure 3:
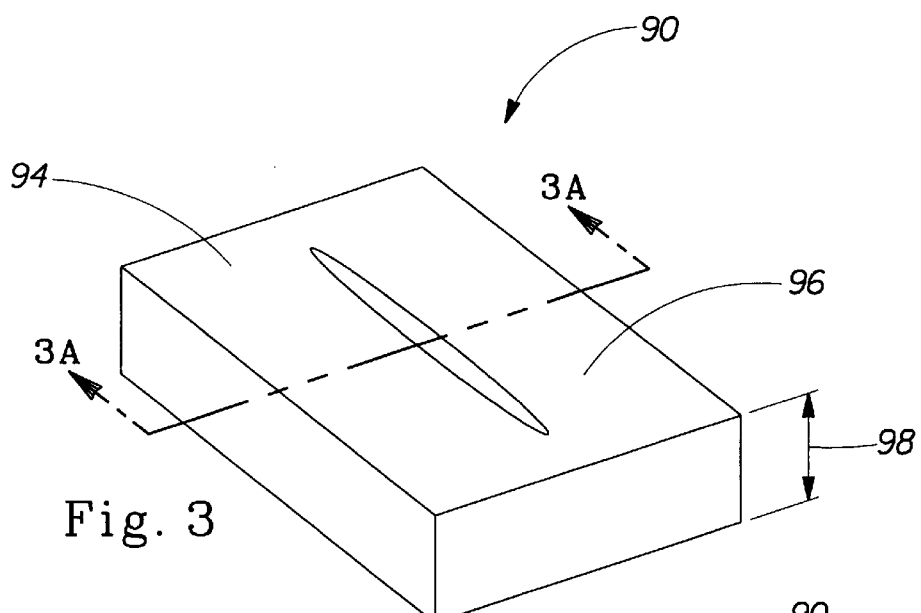
FIG. 3 shows a perspective view of one embodiment of FIG. 2 after activation.
Figure 3A:
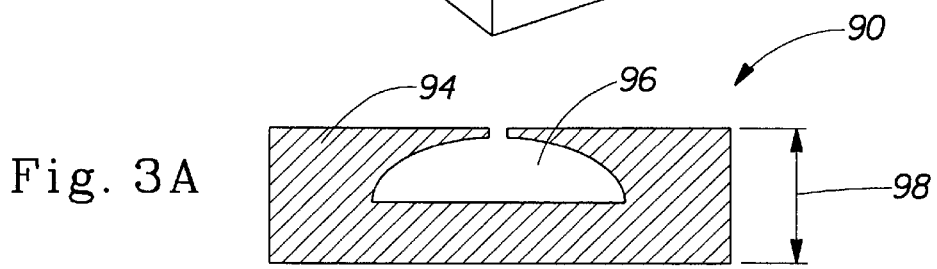
FIG. 3A shows a sectional view of FIG. 3 taken along line 3A—3A of FIG. 3.
Figure 4:
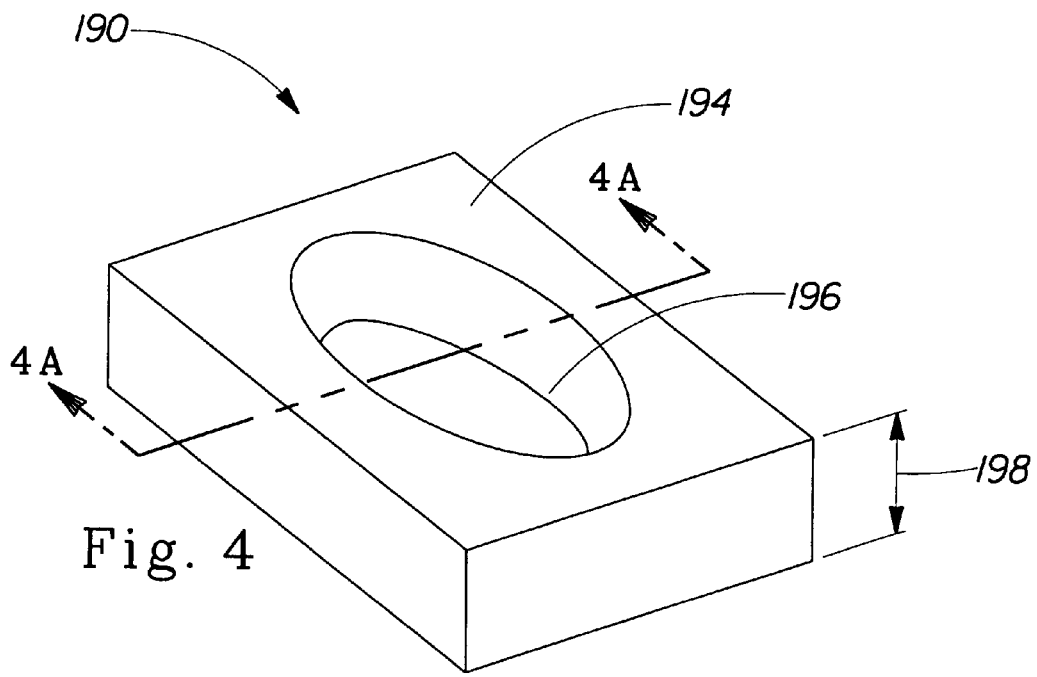
FIG. 4 shows a perspective view of an alternative embodiment of FIG. 2 after activation.
Figure 4A:
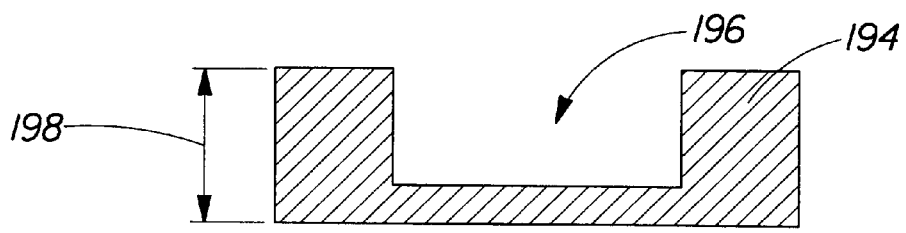
FIG. 4A shows a sectional view of FIG. 4 taken along line 4A—4A of FIG. 4.
Figure 5:
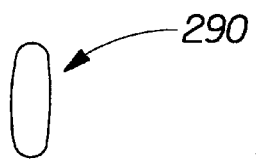
FIG. 5 shows a perspective view of an embodiment of the present invention including a soluble capsule.

The article shown in FIGS. 2 and 2A includes an actuator that comprises a compressed foam spacer 94 vacuum sealed under a water soluble film 94 (e.g., a PVA film). Upon receipt of the proper signal from the proactive sensor, the actuator closes a switch that releases a small amount of stored water to contact and dissolve the water soluble film. This results in the release of the stored mechanical energy in the compressed foam. The foam expands and forms a spacer to provide void volume for the incipient feces. Alternatively, the switch closure may release two chemicals that combine and create a foaming system, which may protectively coat the skin and/or engulf the feces when excreted. Similar systems to prepare for imminent urination events are also included in the scope of this invention.

In another embodiment, the responsive system may include an actuator that alerts the caretaker or the wearer of an impending event such as a defecation or a urination. If the responsive system alerts the caretaker, for example, the caretaker may prepare to change the article to minimize the amount of time that the bodily waste is in contact with the skin of the wearer, may ensure that a bedpan or an absorbent article is in place to contain the bodily waste when it is eliminated, or may aid the wearer in getting to the bathroom before the elimination of the bodily waste. If the responsive system alerts the wearer, alternatively, the responsive system may act as a signaling device that alerts the wearer of an impending defecation or urination before the actual event.

While particular embodiments of the present invention have been illustrated and described, it would be obvious to those skilled in the art that various other changes and modifications can be made without departing from the spirit and scope of the invention. For example, although the present invention is illustrated and described primarily with respect to a disposable diaper, the present invention is not limited to this embodiment. The present invention may also be used, for example, in articles that are applied directly to a wearer (e.g., to the perianal or perineal regions of the wearer) prior to the application of a disposable diaper or in place of a disposable diaper, in a pull-on diaper, a diaper insert, a sanitary napkin, a tampon, etc. It is therefore intended to cover in the appended claims all such changes and modifications that are within the scope of this invention.

What is claimed is:

1. A disposable article to be fitted to a wearer comprising:
   (a) a responsive system including
      (i) a sensor operatively connected to said article, said sensor being adapted to detect an input that correlates to an impending elimination of bodily waste; and
      (ii) an actuator operatively connected to said sensor, said actuator being adapted to perform a responsive function when said sensor detects said input.

2. The disposable article of claim 1, wherein said elimination of bodily waste is a defecation.

3. The disposable article of claim 1, wherein said elimination is a urination.

4. The disposable article of claim 1, wherein said elimination is a discharge of menses.

5. The disposable article of claim 1, wherein said input is one or more of the group selected from a change in pressure, a gas concentration, a moisture, an enzyme a temperature, a motion, and a separation of buttocks.

6. The disposable article of claim 1, wherein said sensor detects changes in electrical activity of sphincter muscles.

7. The disposable article of claim 6, wherein said sphincter muscles include an external anal sphincter.

8. The disposable article of claim 6, wherein said sensor comprises at least two active electrodes and at least one reference electrode.

9. The disposable article of claim 1 further comprising an actuator that performs a responsive function when said sensor detects said input.

10. The disposable article of claim 9, wherein said responsive function is a signal to the caretaker.

11. The disposable article of claim 9, wherein said responsive function is a signal to the wearer.

12. The disposable article of claim 9, wherein said actuator transforms a potential energy to perform said responsive function, said potential energy being one or more selected from the group of mechanical energy, electrical energy, chemical energy.

13. The disposable article of claim 9, wherein said responsive function is one or more selected from the group of creating a void volume, treating skin, creating a foaming system and signaling a caregiver.

14. The disposable article of claim 1, wherein said sensor is integral with said article.

15. The disposable article of claim 1, wherein said sensor is separate from said article.

16. The disposable article of claim 1, wherein said sensor is part of a sensing system.

17. The disposable absorbent article of claim 1, wherein said input is a pressure.

18. The disposable absorbent article of claim 1, wherein said input is an electrical signal.

19. The disposable article of claim 1 further comprising a receiver.

20. The disposable article of claim 19, wherein said receiver is integral with said article.

21. The disposable article of claim 19, wherein said receiver is separate from said article.

22. The disposable article of claim 19 further comprising a transmitter.

23. The disposable article of claim 22, wherein said transmitter comprises an infrared telemetry transmitter.

24. The disposable article of claim 1, wherein said input is one or more of the group selected from an electrical activity, a biological activity and a chemical activity.

25. A disposable absorbent article comprising:
   (a) a topsheet;
   (b) a liquid impermeable backsheet having a body-facing surface and a garment-facing surface, said backsheet being joined to at least a portion of said topsheet;
   (c) an absorbent core disposed between said topsheet and said backsheet; and
   (d) a sensor joined to said article, said sensor being adapted to detect an input that correlates to an impending event.

26. The disposable absorbent article of claim 25, wherein said impending event is an elimination of bodily waste.

27. A disposable article to be fitted to a wearer having an external anal sphincter comprising:
   (a) an electrical sensor operatively connected to said article, said sensor adapted to be attached to the external anal sphincter of the wearer for detecting electrical signals that correlate to an impending elimination of bodily waste; and
   (b) an actuator operatively connected to said sensor, said actuator adapted to perform a responsive function when said sensor detects said impending elimination of bodily waste.

28. The disposable article of claim 27, wherein said sensor includes at least a first, a second and a third electrodes, said first electrode comprising a reference electrode and said second electrode comprising active electrodes in order to allow for a bimodal electrical pickup.

29. The disposable article of claim 27, wherein said actuator includes providing a void space for bodily waste.

* * * * *

UNITED STATES PATENT AND TRADEMARK OFFICE
CERTIFICATE OF CORRECTION

PATENT NO. : 6,149,636
DATED : November 21, 2000
INVENTOR(S) : Donald C. Roe et al.

It is certified that error appears in the above-identified patent and that said Letters Patent is hereby corrected as shown below:

Column 21,
Line 56, delete "finction" and insert -- function --.

Signed and Sealed this

Thirty-first Day of January, 2006

JON W. DUDAS
*Director of the United States Patent and Trademark Office*